United States Patent [19]

Colburn

[11] 4,160,622

[45] Jul. 10, 1979

[54] PORTABLE WATER SAMPLING APPARATUS

[75] Inventor: Edward N. Colburn, Minneapolis, Minn.

[73] Assignee: UOP Inc., Des Plaines, Ill.

[21] Appl. No.: 815,874

[22] Filed: Jul. 14, 1977

[51] Int. Cl.$^2$ .............................................. F04F 5/44
[52] U.S. Cl. .................................. 417/181; 166/264; 417/234
[58] Field of Search ...................... 417/151, 181, 234; 166/264, 105, 105.1, 105.2, 105.3, 105.4, 105.5, 105.6

[56] References Cited

U.S. PATENT DOCUMENTS

| | | | |
|---|---|---|---|
| 46,931 | 3/1865 | Pease | 417/151 |
| 47,399 | 4/1865 | Crooker | 417/151 |
| 1,000,669 | 8/1911 | Cooper | 417/151 |
| 1,333,713 | 3/1920 | Hopkins | 417/151 |
| 1,643,025 | 9/1927 | Meggenhofen | 417/181 |
| 1,982,259 | 11/1934 | Martin | 417/181 X |
| 2,154,773 | 4/1939 | Reed | 417/181 X |
| 2,798,435 | 7/1957 | Armstrong | 417/234 X |
| 2,946,565 | 7/1960 | Williams | 166/264 |
| 3,930,754 | 1/1976 | Mogg et al. | 417/108 |

*Primary Examiner*—Carlton R. Croyle
*Assistant Examiner*—Edward Look

*Attorney, Agent, or Firm*—James R. Hoatson, Jr.; Barry L. Clark; William H. Page, II

[57] ABSTRACT

Portable, self-powered water pumping apparatus for use in sampling water in remotely located wells comprises a wheeled hose reel cart which supports a long length of co-extruded plastic hose or tubing. The co-extrusion comprises a small diameter portion of tubing attached by a web to a large diameter portion of tubing. The smaller diameter tubing is connected to a pressurized cylinder of gas such as a standard 14 oz. propane gas cylinder. A generally J-shaped piece of metal tubing projects from the inside of the smaller tubing, which it frictionally engages, into the center of the larger tubing at the lower end thereof. When the lower ends of the tubes are well submerged beneath the water level in a well, admission of gas to the smaller tube at its upper end will force water which enters the larger tubing in the annular space surrounding the metal tubing up through the larger tube and out the upper end of the larger tube so that it can be collected. To facilitate the insertion of the extruded tubing into a well from the coil in which it is stored, the tubing is formed of a plastic such as a vinyl and acetate modified polyethylene which has a memory and which is flexible at low temperatures. Preferably, the tubing is permitted to lay straight for several days following extrusion. A weight is also hung from the lower end of the plastic tubing to facilitate its entry into a well.

4 Claims, 3 Drawing Figures

PORTABLE WATER SAMPLING APPARATUS

BACKGROUND OF THE INVENTION

The invention is an improvement on the invention disclosed in U.S. Pat. No. 3,930,754 and relates to sampling devices and particularly to devices for sampling water from remotely located wells such as nonactive wells and observation wells as well as from new wells. It is common to place small diameter observation wells of about 2 or 3 inch diameter in a uniform pattern around much larger diameter water producing wells and in the same aquifer. By analyzing the drawdown of the observation wells in response to the drawdown of the pumping well, the permeability and transmissibility of the aquifer as well as its coefficient of storage, can be calculated. It is also important to sample the water in the observation wells to detect possible or potential contamination of the pumped well. Observation wells are also used in connection with injection wells wherein dangerous polluting liquids such as acids are injected into the earth to dispose of them. By taking periodic samples from observation wells in the vicinity of the injection well it is possible to determine if the pollutants are being contained as desired or whether they are spreading to a degree where they could contaminate water wells in the general area.

As a rule, the small observation wells or other wells which one might wish water samples from are situated in realtively remote locations which are inaccessible to sources of power for pumping up water samples. It would be desirable to have a low cost, self-powered, light weight piece of sampling equipment which could be easily carried to the job site in a utility vehicle rather than have to bring in heavy air compressors, generators or other bulky, expensive equipment for powering an air lift or other form of pump. Although the aforementioned U.S. Pat. No. 3,930,754 discloses such a piece of sampling equipment, the coaxial plastic tubes utilized in the patented device are quite difficult to assemble.

SUMMARY OF THE INVENTION

The invention basically comprises a pair of integrally connected, side-by-side, long flexible plastic tubes which may be wound around a reel which is preferably mounted for rotation on a mobile cart and which can be easily manually moved to the site of the well to be sampled. The smaller tubing portion may, for example, have an inner diameter of about 0.12" while the larger diameter tubing may, for example, have an inner diameter of 0.33". The tube portions are connected by an integral web portion. The tubing is wound on the reel so that the upper end thereof is positioned so as to project through the side of the reel a sufficient distance from the reel hub to permit the outer end of the larger diameter tube portion to discharge pumped water into a container. The projecting portion of the smaller diameter tubing projects sufficiently far from the reel hub and larger tubing portion to facilitate the connection thereof to a gas cylinder and valve such as the universally available type used with a propane blow torch or a camp stove. To this end, the upper end of the composite tubing is split along a short length of the connecting web. The major portion of the tubing is wound about the reel for convenience in transporting it to a well and to simplify the lowering of the free end thereof into the well. Since the tubing assumes a limited degree of curvature when it is wound on the reel, a weight is preferably hung from its lower free end to help straighten out the tubing and facilitate its insertion into a well casing. The weight may be attached to a J-shaped piece of metal tubing having an O.D. of about 0.1875" which has its short leg forced into the small tube (after the tube has been heated) and its long leg positioned inside the larger tube. An annular space between the long leg of the metal tubing and the I.D. of the larger tube is maintained to permit the entry of the well water sample which is to be pumped upwardly.

In order to facilitate the sampling of water at low temperatures, the tubing should be made of a material having an elephantine memory which is not brittle and which will straighten out relatively easily when uncoiled into a well casing. A polyethylene stabilized by additions of vinyl and acetate, such as EVA polyethylene made by DuPont, works very well in this respect, especially when it is extruded straight and permitted to lie in repose in a straight form for about a week before it is coiled for handling and shipment.

DESCRIPTION OF THE PREFERRED EMBODIMENT

Figures 1, 2, 3:
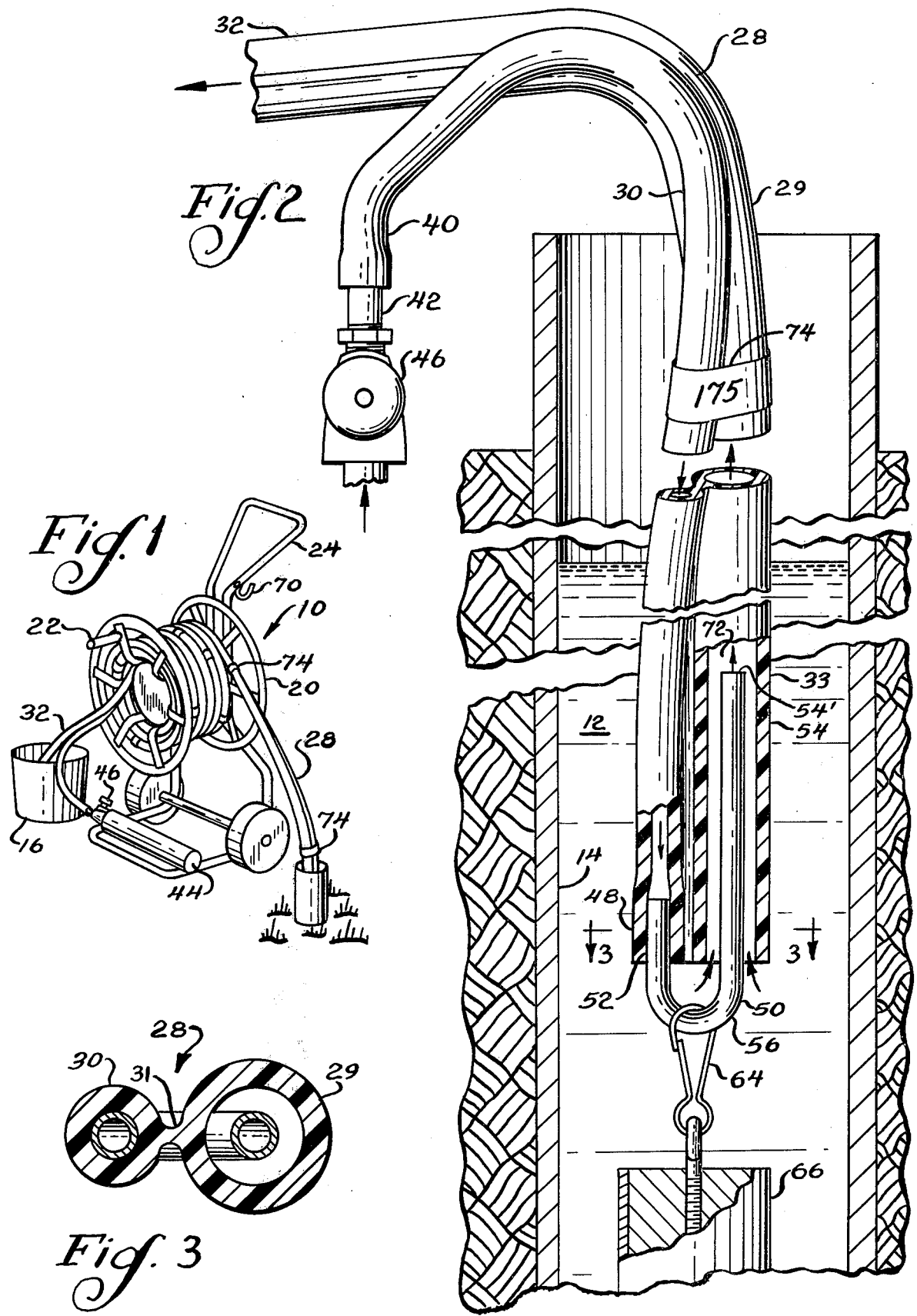
FIG. 1 is a perspective view showing the water sampling apparatus in operation.
FIG. 2 is a partially sectioned, fragmentary view of the gas and water carrying sampling tubes and their relation to a well casing.
FIG. 3 is a cross-sectional view taken on line 3—3 of FIG. 2.

The portable water sampling apparatus indicated generally at 10 is adapted to draw a sample of water 12 from within the well casing 14 and deliver it to a sample container 16. The sampling apparatus includes a hose reel 20 adapted to be rotated by a handle 22. The reel 20 is mounted for rotation on mobile cart 24 which has wheels to facilitate its movement over rough terrain. Wound about the reel 20 is a long length of co-extruded tubing 28 which may be formed of polyethylene or other suitable material. The tubing 28 includes a large diameter portion 29 connected to a small diameter portion 30 by a web portion 31. The tubing portion 29 has an upper end portion 32 from which water samples may be dispersed to a sample container 16, and a lower end portion 33 which is submerged beneath the level of water 12 in the well casing 14. Joined to the large diameter portion 29 for the major portion of its length is the small diameter portion 30. The upper end 40 of the small tube portion 30 is preferably pressed over a nozzle 42 threaded onto a gas cylinder 44 having a gas valve 46. Although the cylinder 44 could contain air, nitrogen or other low cost gas, it is generally more convenient to utilize small disposable cylinders of butane or propane gas which are readily available for use in blow torches and camp stoves. The lower end 48 of the small tube portion 30 communicates with the lower end 33 of the large tube portion 29 by means of a J-shaped connector member 50 which may be made of metal or a suitable plastic.

The J-shaped connector 50 includes a short leg 52 and a long leg 54 joined by a U-shaped portion 56. The connector 50 could be other than J-shaped but the "J" configuration has been found most useful since a relatively short length of the connector (about 1½ inches) forced into the tube portion 48 will frictionally anchor the connector to the tubing 29. A longer length of connector (about 4-8 inches) is necessary inside the large diameter tubing portion 33 in order to insure that the gas from cylinder 44 which moves upwardly through the connector leg 54 will continue upwardly in the tube portion 29 to carry water ahead of it into the collector 16 rather than bubble downwardly around the connector leg 54 and out the lower end of the tubing 29 where its effectiveness would be lost.

A small weight 66 (about 3-5 pounds) is preferably suspended by a hook member 64 from connector loop portion 50. The weight 66 may comprise a short length of tubing filled with lead. The weight facilitates the lowering of the normally coiled tubing 29 into the well casing 14. To prevent any distortion of the tubing 29 while it is being transported, the weight 66 is preferably hooked onto a hook member 70 on the handle of the mobile cart 24.

In operation, the weight 66 and the tubing 29 attached to it are lowered into the well casing 14 a sufficient distance to permit air lift pumping. With this type of pumping the minimum operating submergence is approximately 20% of the depth of the water inlet and approximately 30% or greater submergence is preferred for reasonable production of water. Assuming the gas exit opening 54' from the upper end of connector leg 54 is sufficiently submerged to permit pumping to take place, the valve 46 on the gas cylinder 44 is opened to permit gas to pass down through the small tube 30 and out through the upper end opening 54' of connector leg 54 where it will force the water in the space 72 upwardly through the larger tube portion 29 and out the end portion 32 into the container 16. If the opening 54' is not sufficiently submerged, no water will be pumped but gas will come to the surface. If the gas is butane or propane it will, of course, have an odor which may be detected so that the operator will know that the intake opening 54' is not sufficiently submerged. Commercially available propane cylinders generally have a pressure of 120 to 140 psi when new and warm which is generally sufficient to lift several gallons of water. For example, in one test where the ambient temperature was 75° F., the static water level was 76 feet and the sample intake was at 109 feet, a single 14 ounce propane cylinder was able to lift a total of 8.6 gallons of water before its contents were exhausted. Since the gas cylinder must have a substantial pressure in order to pump water it is possible that a particular gas cylinder will still have a sufficient charge remaining for blow torch or other use if the valve 46 is turned off as soon as the pumping rate decreases substantially. Since the gas cylinder 44 will exert a higher pressure when warm than when cold it is good practice in cold weather to keep the cylinder at room temperature until just before use. The depth of insertion of the tubing in a well can be easily determined by observing depth markers 74 positioned at uniform intervals along the length of the tubing.

I claim as my invention:

1. A portable water pumping apparatus for sampling water from a well comprising a wound coil of elongated, flexible tubing which is normally stored on a hose reel mounted for rotation on a wheeled cart, said flexible tubing being made of a plastic which has a memory and which has been extruded straight and maintained straight for at least several days prior to coiling, said tubing consisting of a pair of parallel arranged small and large diameter tubing portions integrally joined by a web portion; connector means insertable in the upper end of said small diameter tubing portion and having a threaded portion adapted to engage the threaded portion of a cylinder of pressurized gas; a J-shaped connector formed of a short length of hollow tubing and having its shorter leg inserted in frictional engagement with the inside of said small diameter tubing portion at the lower end thereof, the longer leg having a length of at least 4 inches positioned in the adjacent lower end of said large diameter tubing portion but annularly spaced from the inner walls thereof; a weight member removably suspended from said J-shaped connector; the upper end of said large diameter tubing portion comprising a discharge opening means for discharging water forced up through said annular space and said large diameter tubing portion by gas passing down through the small diameter tubing portion and J-shaped connector from said cylinder when at least a portion of said coil of tubing is unwound and the lower end portion of each tubing portion and the top of the J-shaped connector is submerged beneath the water in a well.

2. The water pumping apparatus of claim 1 wherein said plastic is a polyethylene stabilized by additions of vinyl and acetate.

3. The water pumping apparatus of claim 1 wherein said tubing has depth markers positioned along its length.

4. The water pumping apparatus of claim 1 wherein said web portion is split adjacent the upper end of said flexible tubing to separate the small and large diameter tubing portions and facilitate the attachment of a gas cylinder to the small diameter portion and the collection of water samples from the large diameter portion.

* * * * *